(12) United States Patent
Alvi et al.

(10) Patent No.: US 7,767,419 B2
(45) Date of Patent: Aug. 3, 2010

(54) CALIBRATOR FOR NT-PROBNP IMMUNOASSAY

(75) Inventors: Azhar Alvi, Mississauga (CA); William Yajima, Edmonton (CA); Roshana Sikora, Mississauga (CA); George Jackowski, Kettleby (CA); Mee-Ra Hong, Mississauga (CA)

(73) Assignee: Nexus DX, Inc., San Diego, CA (US)

( * ) Notice: Subject to any disclaimer, the term of this patent is extended or adjusted under 35 U.S.C. 154(b) by 414 days.

(21) Appl. No.: 10/359,028

(22) Filed: Feb. 4, 2003

(65) Prior Publication Data

US 2004/0152128 A1 Aug. 5, 2004

(51) Int. Cl.
- C12N 15/12 (2006.01)
- C12N 15/63 (2006.01)
- C12N 15/70 (2006.01)
- C12P 19/34 (2006.01)
- G01N 33/531 (2006.01)
- C07H 21/04 (2006.01)

(52) U.S. Cl. ............... 435/69.3; 435/6; 435/7.1; 435/7.94; 435/71.2; 435/91.1; 435/471; 435/488; 435/320.1; 436/518; 436/536; 436/543; 436/8; 436/811; 530/324; 530/806; 536/23.5

(58) Field of Classification Search ............ 436/518, 436/536, 8, 811, 543; 435/6, 7.1, 7.94, 69.3, 435/71.2, 91.1, 471, 488, 320.1; 530/324, 530/806; 536/23.5
See application file for complete search history.

(56) References Cited

U.S. PATENT DOCUMENTS 5,200,341 A * 4/1993 Obukowicz ............ 435/252.33

FOREIGN PATENT DOCUMENTS

| WO | 89/12069 | * 12/1989 |
|----|----------|-----------|
| WO | 00/45176 | * 8/2000 |

OTHER PUBLICATIONS

Karl et al., 1999. Development of a novel, N-terminal-proBNP (NT-proBNP) assay with a low detection limit. Scand. J. Clin. Lab. Invest. 59 (suppl. 230): 177-181.*

Maurer et al., 1980. Proteins and polypeptides as antigens. Meth. Enzymology 70: 49-70.*

P. Hunt et al, "Immunoreactive amino-terminal pro-brain natriuretic peptide (NT-PROBNP): a new marker of cardiac impairment", Clinical Endocrinology, 47:287-296 (1997).

A. Clerico et al, "Measurement of cardiac natriuretic hormones (atrial natriuretic peptide, brain natriuretic peptide, and related peptides) in clinical practice: the need for a new generation of immunoassay methods", Clinical Chemistry, 46(10):1529-1534 (2000).

F. Boomsma et al, "Plasma A- and B-type natriuretic peptides: physiology, methodology and clinical use", Cardiovascular Research, 51:442-449 (2001).

D. Campbell et al, "Plasma amino-terminal pro-brain natriuretic peptide levels in subjects presenting to the emergency department with suspected acute coronary syndrome: possible role in selecting patients for follow up?", Internal Medicine Journal, 31:211-219 (2001).

A. De Bold et al, "A rapid and potent natriuretic response to intravenous injection of atrial myocardial extract in rats", Life Sciences, 28(1):89-94 (1981).

G. Gross et al, "RNA primary sequence or secondary structure in the translational initiation region controls expression of two variant interferon-beta genes in *Escherichia coli*", Journal of Biological Chemistry, 265 (29):17627-17636 (Oct. 1990).

F. Hobbs et al, "Reliability of N-terminal pro-brain natriuretic peptide assay in diagnosis of heart failure: cohort study in representative and high risk community populations", BMJ, 324:1-5 (Jun. 2002).

P. Hunt et al, "The amino-terminal portion of pro-brain natriuretic peptide (pro-BNP) circulates in human plasma", Biochemical and Biophysical Research Communications, 214(3):1175-1183 (Sep. 1995).

P. Selvais et al, "Cardiac natriuretic peptides for diagnosis and risk stratification in heart failure: influences of left ventricular dysfunction and coronary artery disease on cardiac hormonal activation", European Journal of Clinical Investigation, 28:636-642 (1998).

D. Hughes et al, "An immunoluminometric assay for N-terminal pro-brain natriuretic peptide: development of a test for left ventricular dysfunction", Clinical Science, 96:373-380 (1999).

A. Luchner et al, "N-terminal pro-brain natriuretic peptide after myocardial infarction a marker of cardio-renal function", Hypertension, 39:99-104 (2002).

J. Mair et al, "The impact of cardiac natriuretic peptide determination on the diagnosis and management of heart failure", Clin Chem Lab Med, 39(7):571-588 (2001).

T. McDonagh et al, "Left ventricular dysfunction, natriuretic peptides, and mortality in an urban population", Heart, 86:21-26 (2001).

T. McDonagh et al, "Biochemical detection of left-ventricular systolic dysfunction", The Lancet, 351:9-13 (Jan. 1998).

J. Nilsson et al, "Left ventricular remodeling in the first year after acute myocardial infarction and the predictive value of N-terminal pro brain natriuretic peptide", Am Heart J., 143:696-702 (2002).

A. Richards et al, "Plasma N-terminal pro-brain natriuretic peptide and adrenomedullin—new neurohormonal predictors of left ventricular functino and prognosis after myocardial infarction", Circulation, 97:1921-1929 (1998).

A. Richards et al, "Plasma N-terminal pro-brain natriuretic peptide and adrenomedullin—prognostic utility and prediction of benefit from carvedilol in chronic ischemic left ventricular dysfunction", Journal of the American College of Cardiology, 37(7):1781-1787 (2001).

(Continued)

Primary Examiner—Ann Y. Lam
Assistant Examiner—James L Grun
(74) Attorney, Agent, or Firm—Cooley Godward Kronish LLP

(57) ABSTRACT

The invention provides a method to efficiently express high levels of a recombinant untagged NT-proBNP for use as a calibrator in NT-proBNP immunoassays.

5 Claims, 11 Drawing Sheets

OTHER PUBLICATIONS

G. Sagnella, "Measurement and importance of plasma brain natriuretic peptide and related peptides", Ann Clin Biochem, 38:83-93 (2001).

H. Schulz et al, "Radioimmunoassay for N-terminal probrain natriuretic peptide in human plasma", Scand J Clin Lab Invest., 61:33-42 (2001).

M. Sprengart et al, "The downstream box: an efficient and independent translation initiation signal in *Escherichia coli*", The EMBO Journal, 15(3):665-674 (1996).

C. Stenstrom et al, "Cooperative effects by the initiation codon and its flanking regions on translation initiation", Gene, 273:259-265 (2001).

S. Talwar et al, "Plasma N-terminal pro-brain natriuretic peptide and the ECG in the assessment of left-ventricular systolic dysfunction in a high risk population", European Heart Journal, 20:1736-1744 (1999).

R. Troughton et al, "Treatment of heart failure guided by plasma aminoterminal brain natriuretic peptide", Lancet, 355:1126-1130 (Apr. 2000).

T. Omland et al, "Plasma cardiac natriuretic peptide determination as a screening test for the detection of patients with mild left ventricular impairment", Heart, 76(3):232-237 (Sep. 1996) (Abstract only).

M. Hystad et al, "Regional cardiac expression and concentration of natriuretic peptides in patients with severe chronic heart failure", Acta Physiol Scand., 171(4):395-403 (Apr. 2001) (Abstract only).

T. Sudoh et al, "Cloning and sequence analysis of cDNA encoding a precursor for human brain natriuretic peptide", Biochem Biophy Res Commun., 159(3):1427-1434 (Mar. 1989) (Abstract only).

K. Curry et al, "Effect of ribosome binding site on gene expression in *Escherichia coli*", DNA, 7(3):173-179 (Apr. 1988) (Abstract only).

\* cited by examiner

Figure 1:
NTBNP (mutagenized N-terminal base pairs, prior to deletion of first 2 codons)
NTBNP (mut –2, mutagenized N-terminal bases, lacking first 2 codons.)
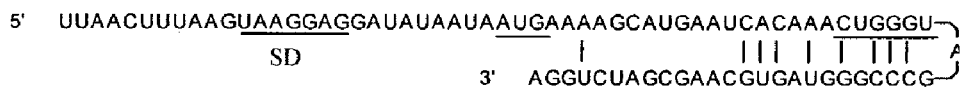

Figure 2: 20% SDS PAGE Coomassie
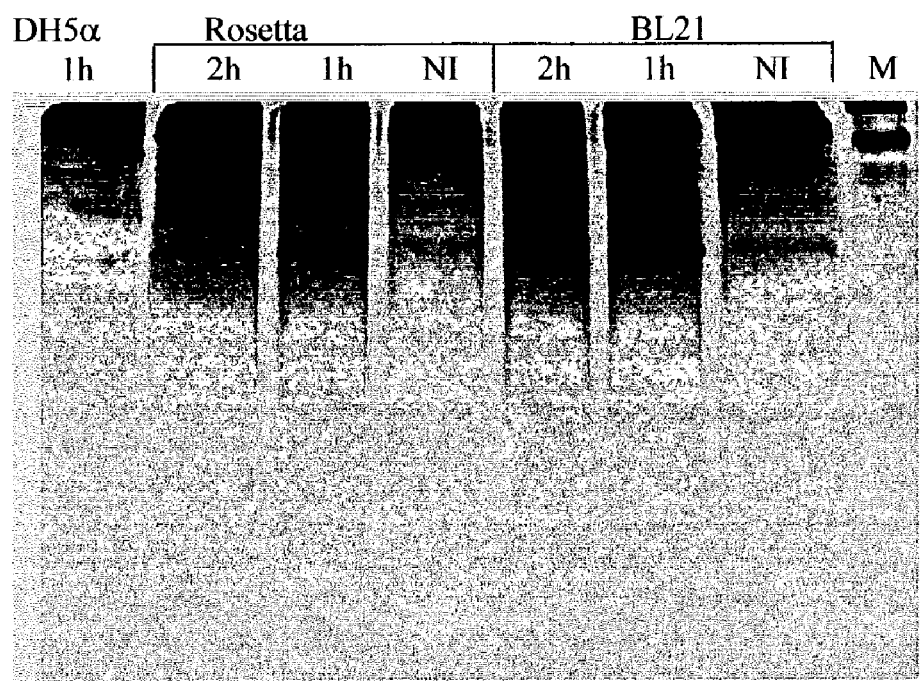
Expression pattern of NT-BNP (mut):

Figure 3: 20% SDS PAGE Western
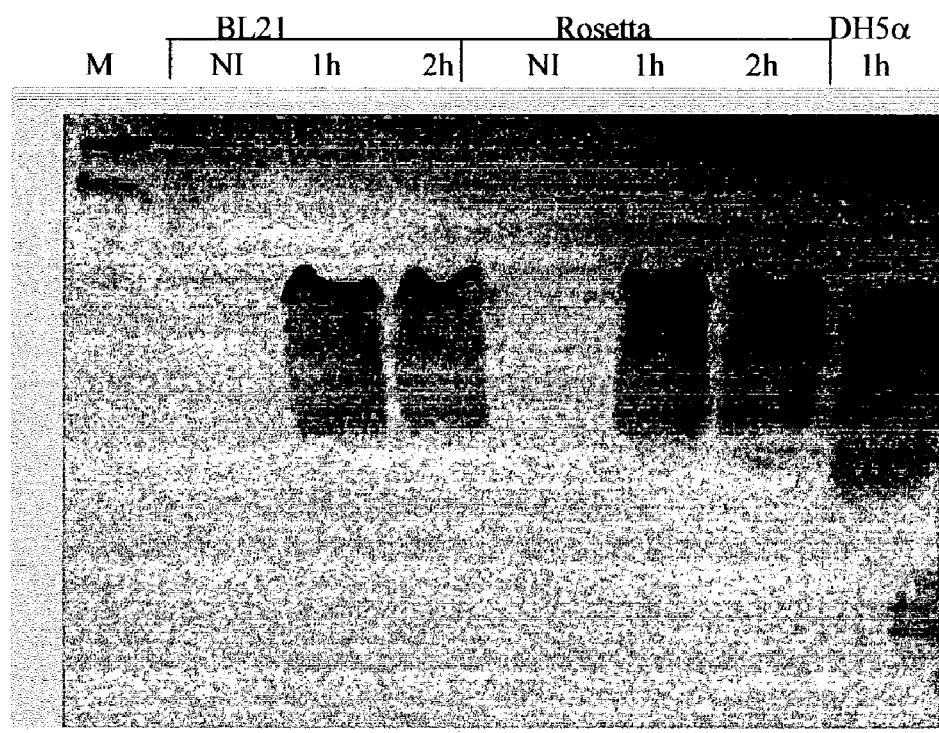
Expression pattern of NT-BNP (mut):

Figure 4:

cDNA sequence of NT-BNP (mutagenized)

```
Epsilon      Shine Dalgarno                              NTBNP (mut-2)
TTAACTTTAAGTAAGGAGGATATAATAATGAAAAGCATGAATCACAAACTGGGTAGCCCGGGTAGTG
CAAGCGATCTGGAAACGTCCGGGTTACAGGAGCAGCGCAACCATTTGCAGGGCAAACTGTCGGAGCTG
CAGGTGGAGCAGACATCCCTGGAGCCCCTCCAGGAGAGCCCCCGTCCCACAGGTGTCTGGAAGTCCCG
GGAGGTAGCCACCGAGGGCATCCGTGGGCACCGCAAAATGGTCCTCTACACCCTGCGGGCACCACGAT
AA
```

Figure 5:

Protein Sequence of NT-BNP (mutagenized)

MKSMNHKLGSPGSASDLETSGLQEQRNHLQGKLSELQVEQTSLEPLQESPRPTGVWKSREVATEGIRGHRK
MVLYTLRAPR.

Expression pattern of rUBNP

20% SDS PAGE Coomassie Staining

← NT-BNP (mut-2)

Purified rUBNP

20% SDS PAGE Silver Stain

NT-BNP (mut-2) →

Purified rUBNP

Mass Spectroscopy Sequencing

SEQUENCE LISTING

```
<160> NUMBER OF SEQ ID NOS: 9

<210> SEQ ID NO 1
<211> LENGTH: 48
<212> TYPE: DNA
<213> ORGANISM: Bacteriophage T7

<400> SEQUENCE: 1
ttaactttaa gtaaggagga tataataatg aaaagcatga atcacaaa                    48

<210> SEQ ID NO 2
<211> LENGTH: 30
<212> TYPE: DNA
<213> ORGANISM: Homo sapiens

<400> SEQUENCE: 2
ctgggtagcc cgggtagtgc aagcgatctg                                        30

<210> SEQ ID NO 3
<211> LENGTH: 46
<212> TYPE: DNA
<213> ORGANISM: Bacteriophage T7

<400> SEQUENCE: 3
ttaactttaa gaaggagata tacatatggc uagcaugacu ggugga                      46

<210> SEQ ID NO 4
<211> LENGTH: 36
<212> TYPE: DNA
<213> ORGANISM: Homo sapiens

<400> SEQUENCE: 4
cacccgctgg gcagccccgg ttcagcctcg gacttg                                 36

<210> SEQ ID NO 5
<211> LENGTH: 80
<212> TYPE: RNA
<213> ORGANISM: Homo sapiens

<400> SEQUENCE: 5
uuaacuuuaa guaaggagga uauaauaaug aaaagcauga aucacaaaca uccgcugggu       60
aguccgggua gugcaagcga                                                   80

<210> SEQ ID NO 6
<211> LENGTH: 80
<212> TYPE: RNA
<213> ORGANISM: Homo sapiens

<400> SEQUENCE: 6
uuaacuuuaa guaaggagga uauaauaaug aaaagcauga aucacaaaca uccgcugggu       60
aguccgggua gugcaagcga                                                   80
```

-continued

```
<210> SEQ ID NO 7
<211> LENGTH: 80
<212> TYPE: RNA
<213> ORGANISM: Homo sapiens

<400> SEQUENCE: 7
uuaacuuuaa guaaggagga uauaauaaug aaaagcauga aucacaaacu ggguagcccg      60
gguagugcaa gcgaucugga                                                 80

<210> SEQ ID NO 8
<211> LENGTH: 273
<212> TYPE: DNA
<213> ORGANISM: Homo sapiens

<400> SEQUENCE: 8
ttaactttaa gtaaggagga tataataatg aaaagcatga atcacaaact gggtagcccg      60
ggtagtgcaa gcgatctgga aacgtccggg ttacaggagc agcgcaacca tttgcagggc     120
aaactgtcgg agctgcaggt ggagcagaca tccctggagc ccctccagga gagccccgt     180 cccacaggtg tctggaagtc ccgggaggta gccaccgagg gcatccgtgg gcaccgcaaa    240
atggtcctct acaccctgcg ggcaccacga taa                                 273

<210> SEQ ID NO 9
<211> LENGTH: 81
<212> TYPE: PRT
<213> ORGANISM: Homo sapiens

<400> SEQUENCE: 9

Met Lys Ser Met Asn His Lys Leu Gly Ser Pro Gly Ser Ala Ser Asp
1               5                   10                  15

Leu Glu Thr Ser Gly Leu Gln Glu Gln Arg Asn His Leu Gln Gly Lys
            20                  25                  30

Leu Ser Glu Leu Gln Val Glu Gln Thr Ser Leu Glu Pro Leu Gln Glu
        35                  40                  45

Ser Pro Arg Pro Thr Gly Val Trp Lys Ser Arg Glu Val Ala Thr Glu
    50                  55                  60

Gly Ile Arg Gly His Arg Lys Met Val Leu Tyr Thr Leu Arg Ala Pro
65                  70                  75                  80

Arg
```

CALIBRATOR FOR NT-PROBNP IMMUNOASSAY

CROSS REFERENCE TO RELATED APPLICATIONS

This application is related to the following co-pending application Ser. Nos.: 10/299,977 and 10/300,733; both filed on Nov. 18, 2002; the contents of which are each herein incorporated by reference. The instant application discloses a protein calibrator for use in the NT-proBNP immunoassays disclosed in application Ser. Nos. 10/299,977 and 10/300, 733.

FIELD OF THE INVENTION

This invention relates to the expression and purification of proteins, more particularly to the expression and purification of a protein calibrator used for standardization of an immunoassay, and most particularly to the expression and purification of NT-BNP used to calibrate standards in an immunoassay which measures the concentration of NT-proBNP in bodily fluids.

BACKGROUND OF THE INVENTION

B-type natriuretic peptide (brain natriuretic peptide, BNP) belongs to the family of structurally similar, but genetically distinct natriuretic peptides (NPs) first described by de Bold et al. (Proc Soc Exp Biol Med 161:508-511 1979 and Life Science 28:89-94 1981). The NPs are protein hormones which possess potent diuretic, natriuretic and vasodilatory properties and have been reported as valuable diagnostic and prognostic markers in cardiovascular disease, particularly for patients in New York Heart Association (NYHA) classes I-IV congestive heart failure (CHF) (Boomsma et al. Cardiovascular Research 51:442-449 2001).

The human proBNP gene has been cloned by various groups (for example, Sudoh et al. Biochem Biophys Res Commun 159(3):1427-1434 1989). The protein products of the proBNP gene are major diagnostic markers of congestive heart failure. Expression of the BNP protein within the cell (cardiomyocyte) occurs as a 134 amino acid residue preproBNP. Cleavage of the 26 amino acid signal peptide from the N-terminal results in proBNP which is 108 amino acid residues in length. Prior to release into the blood, proBNP-undergoes a final protein processing step where a 32 amino acid C-terminal peptide (BNP-32) is cleaved. BNP-32 is the bioactive hormone. The remaining amino acid residues 1-76 is termed NT-BNP or NT-proBNP. NT-BNP also circulates in the plasma and like BNP is an important marker of ventricular dysfunction (Hunt et al. Biochem Biophys Res Commun 14:1175-1183 1995 and Hunt et al. Clin Endocrinology 47:287-296 1997).

Many studies have demonstrated the clinical utility of measuring plasma concentrations of NPs, including NT-proBNP. NPs have been suggested as the biomarkers of choice for diagnosis and risk stratification of patients with heart failure (Boomsma et al. Cardiovascular Research 51:442-449 2001; Hunt et al. Clin Endocrinology 47:287-296 1997; Clerico et al. Clinical Chemistry 46:1529-1534 2000; Mair et al. Clin Chem Lab Med 39:571-588 2001; Sagnella Ann Clin Biochem 38:83-93 2001; Selvais et al. Eur J Clin Invest 28:636-642 1998; McDonagh et al. Heart 86:21-26 2001). Several studies have shown the utility of using NP measurements to identify patients with left ventricular dysfunction, even amongst patients who are asymptomatic (NYHA class I) and it has been suggested that NP measurements as a screening tool may help effectively target patients within high risk heart failure groups (coronary artery disease, hypertension, diabetes, elderly) who will require follow-up assessment and treatment (Hunt et al. Clin Endocrinology 47:287-296 1997; Hughes et al. Clinical Science 96:373-380 1999; Omland et al. Heart 76:232-237 1996; McDonagh et al. Lancet 351:9-13 1998; Schulz et al. Scand J Clin Lab Invest 61:33-42 2001; Talwar et al. Eur Heart J 20:1736-1744 1999; Hystad et al. Acta Physiol Scand 171:395-403 2001; Hobbs et al. BMJ 324:1498 2002). NPs have been shown to have good prognostic value with regards to both morbidity and mortality in heart failure. Several studies have also demonstrated the utility of NP measurements in the prediction of left ventricular dysfunction and survival following acute myocardial infarction (Richards et al. Circulation 97:1921-1929 1998; Luchner et al. Hypertension 39:99-104 2002; Campbell et al. Intern Med J 31:211-219 2001; Nilsson et al. Am Heart J 143:696-702 2002). Monitoring NP levels may also provide guidance in tailoring therapies to meet the required intensity of the individual patient and in monitoring therapeutic efficacy (Richards et al. J Am Coll Cardiol 37:1781-1787 2001; Troughton et al. Lancet 355:1126-1130 2000).

The NT-proBNP assays disclosed in co-pending application Ser. Nos. 10/299,977 and 10/300,733 employ a sandwich ELISA technique to measure circulating NT-proBNP in human plasma. Such immunoassay techniques provide a quantitative estimate of concentration by direct comparison with a standard material. However, there are no pre-existing reference methods by which to calibrate standards for the majority of analytes determined by immunoassay. In the absence of such reference methods, calibration requires a source of purified analyte (see The Immunoassay Handbook, edited by David Wild, Stockton Press, 1994, especially pages 54-57 for a discussion of calibration and standardization).

In the NT-proBNP immunoassay the purified analyte required is NT-BNP. The production of recombinant NT-proBNP is not easily achieved based upon the short amino acid sequence.

Hunt et al. (Clinical Endocrinology 47:287-295 1997) teaches a method for identification of NT-proBNP in human plasma using a radioimmunoassay technique. A synthetic human peptide of amino acid residues of 1-21 of proBNP was used as a standard in Hunt et alls radioimmunoassay (see FIG. 1 of Hunt et al.).

WO 00/45176 (Karl et al.) discloses a method for recombinant expression of NT-proBNP in bacteria (*E. coli*)using N-terminal histidine tags (see example 1 of Karl et al.). This purified N-terminal proBNP was expressed to be used as a calibrator in the immunoassay methods of Karl et al.

There are some disadvantages to the expression of recombinant proteins using tags. The presence of tags at the N-terminus can alter the three-dimensional conformation and thus alter the biological activity of the protein. Additionally, affinity chromatography is often the purification step when carrying out methods of expression using tagging. The chemicals used in affinity chromatography can also alter the protein conformation and thus the biological activity. It would be advantageous to avoid these problems by utilizing a method for expression of untagged recombinant proteins.

What is lacking in the art is a method to efficiently express high levels of a recombinant untagged NT-proBNP protein capable for use as a calibrator in NT-proBNP immunoassays.

SUMMARY OF THE INVENTION

The instant invention provides a stepwise method to efficiently express high levels of a recombinant untagged NT-proBNP for use as a calibrator in NT-proBNP immunoassays. More particularly, a stepwise method is provided for expression of NT-BNP (N-terminus brain natriuretic peptide)in bacteria comprising:

a) introducing SEQ ID NO:1 at the 5' end of a nucleic acid encoding for NT-BNP;
b) replacing codons 3 through 12 of said nucleic acid encoding for NT-BNP with SEQ ID NO:2;
c) deleting codons 1 and 2 of said nucleic acid encoding for NT-BNP; and
d) transducing a bacterial culture with the nucleic acid of step c wherein said bacterial culture then expresses NT-BNP.

The recombinant NT-proBNP expressed in this stepwise method is then extracted from the bacterial culture and chromatographically purified. The resulting purified NT-BNP is capable of functioning as a calibrator in an immunoassay specific for NT-BNP. A calibrator (in the instant case purified NT-BNP)can be applied as a series of concentration dilutions depending upon the needs of the experimenter within a working range for the analyte of interest, for example (with respect to the instant case), but not limited to, a dilution series of the following concentrations, 0 pg/ml of NT-BNP, 50 pg/ml of NT-BNP, 150 pg/ml of NT-BNP, 375 pg/ml of NT-BNP, 1500 pg/ml of NT-BNP and 3000 pg/ml of NT-BNP.

Accordingly, it is an objective of the instant invention to provide a stepwise method to efficiently express high levels of a recombinant untagged NT-proBNP for use as a calibrator in NT-proBNP immunoassays.

It is a further objective of the instant invention to provide a purified NT-BNP protein capable of functioning as a calibrator in an immunoassay specific for NT-BNP.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 1 shows the formation of secondary structures in NT-BNP mRNA sequences prior to deletion of the first two codons (SEQ ID NOS:5 and 6, top and center) and post deletion of the first two codons (SEQ ID NO:7 bottom).

FIG. 2 shows the expression pattern of NT-BNP mut visualized with coomassie staining after 20% SDS PAGE gel electrophoresis.

FIG. 3 shows the expression pattern of NT-BNP mut visualized using western blotting after 20% SDS PAGE gel electrophoresis.

FIG. 4 shows the cDNA sequence (SEQ ID NO:8) of NT-BNP mut$^{-2}$ (rUBNP).

FIG. 5 shows the protein sequence (SEQ ID NO:9) of NT-BNP mut$^{-2}$ (rUBNP).

DEFINITIONS

Figure 6:
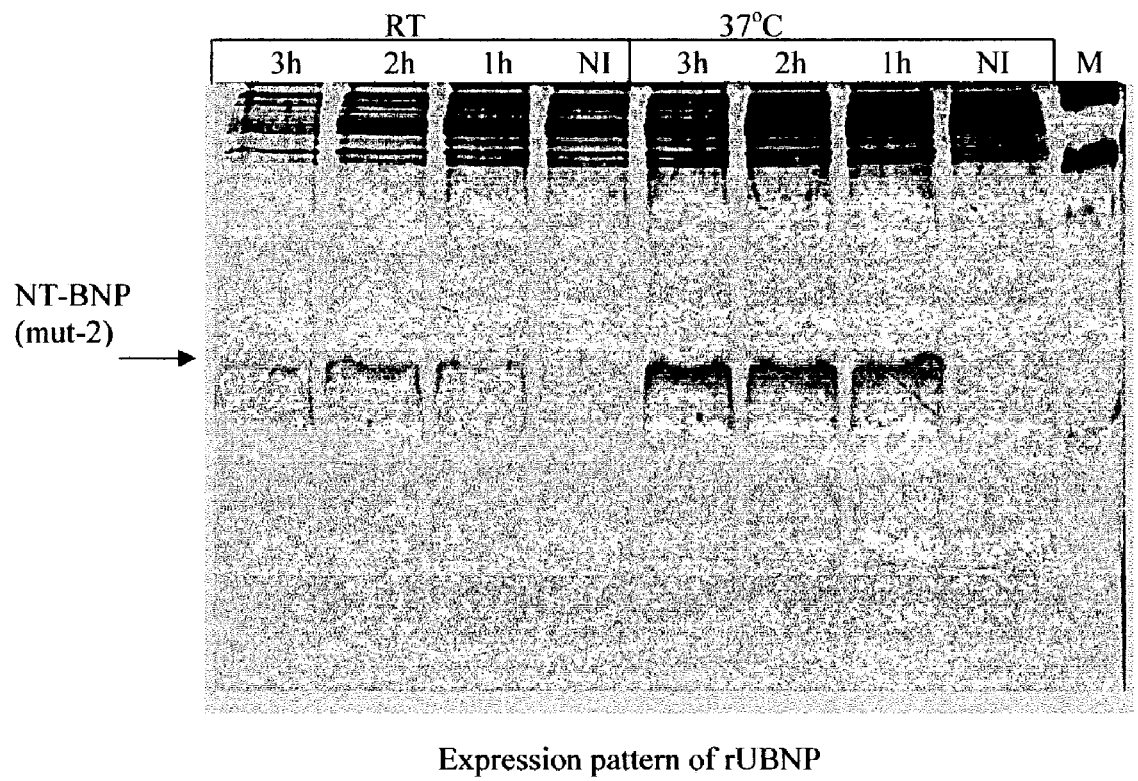
FIG. 6 shows the expression pattern of rUBNP (NT-BNP mut$^{-2}$) visualized with coomassie staining after 20% SDS PAGE gel electrophoresis.

The following list defines terms and phrases used throughout the instant specification.

As used herein the abbreviation "BNP" refers to a B-type natriuretic peptide or protein. "B-type" refers to brain.

As used herein the abbreviation "NT-BNP" or "NT-proBNP" refers to N-terminal brain natriuretic peptide or protein. NT-BNP is the 1-76 amino acid residue hormone remaining after BNP undergoes all processing.

As used herein the abbreviation "preproBNP" refers to the 134 amino acid residue unprocessed brain natriuretic peptide.

As used herein the abbreviation "proBNP" refers to the form of brain natriuretic peptide from which the 26 amino acid residue signal peptide has been cleaved. ProBNP is 108 amino acid residues in length.

As used herein the abbreviation "BNP 32" refers to the bioactive brain natriuretic peptide which is 32 amino acid residues in length. It is formed when proBNP undergoes a final protein processing step where the 32 amino acid C-terminal peptide is cleaved.

As used herein the abbreviation "mut" refers to the mutated form of NT-BNP which results from carrying out cloning steps I-IV. NT-BNP mut has the full 1-76 amino acid residues of NT-BNP. Experiments using NT-BNP mut are shown in FIGS. 2 and 3.

As used herein the abbreviation "rUBNP" refers to recombinant untagged brain natriuretic peptide which results from carrying out cloning steps I-V. The rUBNP protein has amino acid residues 3-76 of NT-BNP. "rUBNP" is also referred to as "NT-BNP mut$^{-2}$", thus the terms "rUBNP" and "NT-BNP mut$^{-2}$" are used interchangeably herein.

The terms "calibrator" "standard" and "reference" are used interchangeably herein.

As used herein the abbreviation "RBS" refers to ribosome binding site.

The terms "initiation codon" and "start codon" are used interchangeably herein.

The terms "codon" and "triplet" are used interchangeably herein.

As used herein the abbreviation "IPTG" refers to isopropyl-β-D-thiogalactopyranoside.

DETAILED DESCRIPTION OF THE INVENTION

Quantitative analysis requires standardization to ensure accurate measurements. Immunoassays do not directly measure analyte concentration but provide a quantitative estimate of concentration by direct comparison with standard (or reference) materials. These standard materials are known as "calibrators" or "standards" and are used to assign values (for example, concentrations) to unknown samples. Usually in diagnostic immunoassays, which provide a quantitative result, a series of six calibrator solutions of different and known concentrations are run prior to unknown samples, then a calibration curve is plotted and the concentration of the unknown samples is determined by interpolation. However, for most of the analytes which are determined in diagnostic immunoassays, there are no known reference materials with which to calibrate standards. In the absence of reference materials, calibration requires the purified analyte to assure correspondence between the calibrator and the analyte tested. In such immunoassays, the purified analyte is also the calibration material. (see The Immunoassay Handbook, edited by David Wild, Stockton Press, 1994, especially pages 54-57 for a discussion of calibration and standardization).

The NT-proBNP assays disclosed in co-pending application Ser. Nos. 10/299,977 and 10/300,733 employ a sandwich ELISA technique to measure circulating NT-proBNP in human plasma. A purified source of NT-BNP is essential for calibration of these immunoassays.

Recognizing the need for a source of NT-BNP in order to calibrate their assay, the instant inventors applied existing molecular information in an innovative manner in order to drive bacterial protein expression to achieve a high level expression of NT-BNP. It has been reported in the literature that the introduction of the epsilon sequence (5'-TTAACTTTA-3') upstream of the Shine-Dalgarno sequence (core sequence, 5'-AGGAGGU-3') along with the introduction of the downstream box following the start codon (ATG) improves the expression of proteins by promoting mRNA/ribosome interaction. A 7-10 nucleotide spacer between the Shine-Dalgarno sequence and the start codon also promotes protein expression. Additionally, the codon choice immediately upstream and downstream of the start codon can promote protein expression(Sprengart et al. EMBO Journal 15(3):665-674 1996; Strenstrom et al. Gene 273:259-265 2001; Curry et al. DNA 7(3):173-179 1988; Rinquist et al. Mol Microbiol 6(9):1219-1229 1992). RNA molecules are usually single stranded, however there are regions of self-complementarity where the RNA molecule forms internal double-stranded regions termed "hairpins". This property of RNA is referred to as RNA secondary structure. RNA hairpins often serve as translation initiation stop signals as the stable hairpin structure disrupts the binding between elements of the translation complex thus promoting disassociation of the complex. The rate of formation of the initiation complex defines how quickly a given protein can be translated. Additionally, the hairpin structure may mask binding sites for elements of the translation complexes (see Hames & Hooper, Instant Notes:Biochemistry, second edition, Springer-Verlag, 2000, for a discussion of RNA secondary structures). It is well known that strong RNA secondary structures involving the Shine-Dalgarno sequence, the start codon, and the 10 amino acid residues following the start codon decrease the chances of translation initiation by directly affecting the ability of the 30s subunit to dock onto the mRNA (see FIG. 1 for examples of RNA secondary structures formed). Researchers have tried to increase protein expression by making modifications to the genetic regions(sequences surrounding the start codon) involved in translation initiation such as those regions noted in the above paragraph.

Various attempts to express high levels of an untagged NT-BNP mut in bacteria were unsuccessful (see FIGS. 2 and 3). Often difficulties in gene expression occur at the level of translation due to inefficient initiation. The efficiency of initiation is affected by the sequences surrounding the start codon. These sequences act cooperatively and often synergistically to increase the efficiency of initiation. Initiation is the rate limiting step of protein synthesis and in bacteria refers to the assembly of a ribosome on an mRNA and requires mRNA interactions to form a ribosome binding site (RBS). Upon correct positioning in the RBS the ribosome is directed to the proper translational start site. Two major elements of the RBS are the initiation codon and the Shine-Dalgarno sequence. The initiation codon is usually AUG but can also be GUG or UUG for a small percentage of bacterial genes. The initiation codon (start codon) is the first codon to be translated into protein. The Shine-Dalgarno sequence is located 8 to 13 nucleotides upstream of the initiation codon and is a purine rich region which contains the core sequence 5'-AGGAGGU-3'. The Shine-Dalgarno sequence is able to form base-pairs (i.e., is complementary to) with the 3'-end of the 16S rRNA in the small subunit of the ribosome and positions the ribosome correctly at the initiation codon.

Other important elements to translation initiation are the epsilon sequence and the downstream box. The epsilon sequence 5'-TTAACTTTA-3' is located upstream of the Shine-Dalgarno sequence and is able to form base-pairs (i.e., is complementary to) with nucleotides 458-466 of the 16S rRNA. The downstream box sequence is a translational enhancer located downstream from the initiation codon and is able to form base-pairs (i.e. is complementary to) with nucleotides 1469-1483 of the 16S rRNA (see Sprengart et al. EMBO Journal 15(3): 665-674 1996 and Turner et al. Instant Notes: Molecular Biology, second edition, Springer-Verlag, 2000; for a discussion of the elements of translation initiation in bacteria).

Sprengart et al. (EMBO Journal 15(3): 665-674 1996) disclose that nucleotide substitutions in the downstream box of the bacteriophage T7 gene 10 translation initiation region result in an increase of expression. Such substitutions are for example, 5'-CATGAATCACAAA-3' (highlighted nucleotides indicate substitutions; sequence represents nucleotides 36-48 of SEQ ID NO:1)as compared to the unmodified sequence 5'-CAUGACUGGUGGA-3' (nucleotides 34-46 of SEQ ID NO:3).

It has been reported in the literature that distance (with regard to the number of bases)between the Shine-Dalgarno sequence and the initiation codon affects translation initiation. The optimal distance for efficiency of initiation is 7-10 nucleotides. Additionally, the codons immediately surrounding the start codon affect the rate of gene expression. The sequence ATAAUGAAA, wherein ATA is the codon immediately preceding the start codon and AAA (or another adenine-rich triplet) immediately proceeds the start codon, shows the greatest expression(see Curry et al. DNA 7(3): 173-179 and Stenstrom et al. Gene 273:259-265 2001).

Ringquist et al. (Mol Microbiol 6(9): 1219-1229 1992) discussed how mutations in the Shine-Dalgarno sequence affect translation and disclosed that the sequence UAAG-GAGG initiated translation approximately four times more efficiently than the core sequence AAGGAG itself. Thus, the addition of a nucleotide (for example, U or T) immediately upstream of the core sequence and the addition of a nucleotide (for example, G) immediately downstream of the core sequence can improve protein expression.

The instant invention is drawn to a stepwise method for expression of NT-BNP (N-terminus brain natriuretic peptide) in bacteria comprising:
a) introducing SEQ ID NO:1 at the 5' end of a nucleic acid encoding for NT-BNP;(step a includes sub-steps I-III)
b) replacing codons 3 through 12 of said nucleic acid encoding for NT-BNP with SEQ ID NO:2; (step b is sub-step IV)
c) deleting codons 1 and 2 of said nucleic acid encoding for NT-BNP; (step c is sub-step V)
d) transducing a bacterial culture with the nucleic acid of step c wherein said bacterial culture then expresses NT-BNP.

The instant inventors used all of the information available in the prior art to design SEQ ID NO:1 (5'-TTAACTTTAAG-TAAGGAGGATATAATAATGAAAAGCAT-GAATCACAAA-3'). SEQ ID NO:1 is a mutated species of the bacteriophage T7 gene 10 translation initiation region and was mutated by carrying out three cloning steps (steps I-III).

Step I included modification of the downstream box according to the method of Sprengart et al. 5'-CATGAATCACAAA-3' (highlighted nucleotides indicate substitutions; sequence represents nucleotides 36-48 of SEQ ID NO:1) is the resulting sequence of step I. Step II included positioning eight nucleotides between the start codon and the Shine-Dalgarno sequence, placing the ATA codon in the position immediately preceeding the start codon (AUG) and placing the AAA in the position immediately proceeding the start codon (AUG) according to the methods of Curry et al. and Stenstrom et al. (DNA 7(3): 173-179 and Gene 273:259-265 2001, respectively). 5'-ATAATGAAA-3' (nucleotides 25-33 of SEQ ID NO:1)is the resulting sequence of step II. Step III included the addition of a nucleotide (for example, U or T) immediately upstream of the core sequence (of the Shine-Dalgarno sequence)and the addition of a nucleotide (for example, G) immediately downstream of the core sequence according to the method of Ringquist et al. 5'-TAAGGAGG-3' (nucleotides 12-19 of SEQ ID NO:1) is the resulting sequence of step III. The mutated bacteriophage T7 gene 10 translation initiation region resulting from cloning steps I-III was added to the 5' region of the nucleic acid encoding NT-BNP.

Step IV of the cloning strategy involves reducing the GC content of the 5' region of the nucleic acid encoding NT-BNP without changing the amino acid sequence in order to suit bacterial codon usage. A codon or triplet is a linear sequence of three adjacent nucleotides which specify a particular amino acid. There are four nucleotide bases, thus there are sixty four possible codons. Only twenty amino acids are specified by the sixty four possible codons, thus many codons are redundant (see Scott & Mercer, Concise Encyclopedia Biochemistry and Molecular Biology, third edition, Walter de Gruyter, Berlin-New York, 1997, see pages 126 and 241 for a discussion of the genetic code). Many organisms have a preference of codon usage, for example if the triplets TCA and AGT both specify serine, one organism may prefer to use TCA to specify serine while a different organism may prefer to use AGT to specify serine. When expressing heterologous recombinant proteins (for example, expression of a human protein in *E. coli*) it is often advantageous to encode the protein using the codons preferred by the host in which the protein is being expressed. Many human proteins have been expressed in *E. coli*, for example, interferon. Gross et al. (Journal of Biological Chemistry 265(29): 17627-17636 1990) disclose expression of human interferon in *E. coli* wherein the interferon is encoded according to *E. coli* codon usage. In the instant case, seven of the first twelve codons of NT-BNP were altered to suit bacterial usage. Codon four was changed from GGC specifying glycine to GGT specifying glycine; codon six was changed from CCC specifying proline to CCG specifying proline; codon eight was changed from TCA specifying serine to AGT specifying serine; codon nine was changed from GCC specifying alanine to GCA specifying alanine; codon ten was changed from TCG specifying serine to AGC specifying serine; codon eleven was changed from GAC specifying asparagine to GAT specifying asparagine and codon twelve was changed from TTG specifying leucine to CTG specifying leucine. Accordingly, codons 3-12 of NT-BNP were replaced with SEQ ID NQ:2 (5'-CTGGGTAGCCCGGGTAGTGCAAGCGATCTG-3') which reflects the changes made to suit bacterial codon preference.

The expression plasmid containing NT-BNP mutated by carrying out the cloning strategy of steps I-IV (NT-BNP mut) was then transfected into bacteria; followed by induction of expression and expression assessment. The mutations in NT-BNP generated by carrying out steps I-IV resulted in very low, expression of NT-BNP mut. Therefore, it was determined that this plasmid was not useful for producing NT-BNP in quantities significant for purification purposes. FIGS. 2 and 3 exemplify these experimental results. It is noted that several different cell lines are used in the experiments described herein in order to show that the recombinant protein expression is not effected by cell type. FIG. 2 shows the expression pattern of NT-BNP mut visualized using coomassie staining after 20% SDS PAGE gel electrophoresis. Pre and post-induction cell lysate samples were loaded onto the gel. Lane 1contains IPTG induced (at 37° C.) samples from DH5α cells. Lanes 2 and 3 contain IPTG induced (at 37° C.) samples from Rosetta cells at time points 2 hours (lane 2) and 1 hour (lane 3). Lane 4 contains a sample from the pre-induction culture of Rosetta cells. Lanes 5 and 6 contain IPTG induced (at 37° C.) samples from BL21 cells at time points 2 hours (lane 5) and 1 hour (lane 6). Lane 7 contains a sample from the pre-induction culture of BL21 cells. Lane 8 contains the kaleidoscope protein marker (BioRad).

FIG. 3 shows the expression pattern of NT-BNP mut using 20% SDS PAGE electrophoresis and Western blotting. Pre and post-induction cell lysates were loaded onto the gel. Lane 1 contains the kaleidoscope marker. Lane 2 contains a sample from the pre-induction culture of BL21 cells. Lanes 3 and 4 contain IPTG induced (at 37° C.) samples from BL21 cells at time points 1 hour (lane 3) and 2 hours (lane 4). Lane 5 contains a sample from the pre-induction culture of Rosetta cells. Lanes 6 and 7 contain IPTG induced (at 37° C.) samples from Rosetta cells at time points 1 hour (lane 6) and 2 hours (lane 7). Lane 8 contains a IPTG induced (at 37° C.) sample from DH5α cells.

Recognizing that this expression plasmid containing NT-BNP mut mutated by carrying out the cloning strategy of steps I-IV was not providing a sufficient quantity of NT-BNP for purification, the instant inventors added a step V to the cloning strategy.

Step V of the cloning strategy involves a mutation to reduce the formation of secondary structures between the Shine-Dalgarno sequence, the start codon, and the 10 amino acid residues following the start codon. It is known that the formation of the secondary structures decrease the chances of translation initiation by directly affecting the ability of the 30s subunit to dock onto the mRNA. In order to reduce the formation of strong secondary structures, the first two codons (encoding two amino acids) were deleted from NT-BNP mut. FIG. 1 shows the formation of secondary structures in NT-BNP mRNA sequences prior to deletion of the first two codons (SEQ ID NOS:5 and 6) and post deletion of the first two codons (SEQ ID NO:7).

The expression plasmid containing NT-BNP mut$^{-2}$ (rUBNP) mutated by carrying out the cloning strategy of steps I-V was then transfected into bacteria; followed by induction of expression and expression assessment. The addition of step V to the cloning strategy significantly enhanced expression of NT-BNP mut$^{-2}$ to levels sufficient for purification purposes. DNA sequencing of the expression plasmid containing NT-BNP mut$^{-2}$ mutated by carrying out the cloning strategy of steps I-V confirmed the presence of all 5 mutations. Therefore, this plasmid is useful for efficient expression of high levels of a recombinant untagged NT-proBNP for purification and use as a calibrator in NT-proBNP immunoassays. FIG. 4 shows the cDNA sequence (SEQ ID NO:8)of NT-BNP mut$^{-2}$. FIG. 5 shows the amino acid (protein sequence; SEQ ID NO:9) sequence of NT-BNP mut$^{-2}$.

In all experimental procedures the expression induction step utilized IPTG. After transfection of the bacterial cultures with the recombinant plasmid, the cultures were treated with IPTG (isopropyl-β-D-thiogalactopyranoside) to induce expression of the NT-BNP. IPTG is a synthetic reagent similar in structure to lactose and is commonly used in a screening method well-known in the art called blue-white screening. IPTG can induce the expression of proteins under the control of the lac operon.

The NT-BNP mut$^{-2}$ or rUBNP (residues 3-76) protein was visualized on a coomassie stained gel after expression induction with IPTG. FIG. 6 exemplifies this result and shows the expression of rUBNP(NT-BNP mut$^{-2}$) visualized with coomassie staining after 20% SDS-PAGE gel electrophoresis. With regard to FIG. 6, pre and post-induction cell lysate samples were loaded onto the gel. Lanes 1-3 contain IPTG induced (at room temperature) samples from time points 3 hours (lane 1), 2 hours (lane 2) and 1 hour (lane 3). Lane 4 contains a pre-induction sample. Lanes 5-7 contain IPTG induced (at 37° C.) samples from time points 3 hours (lane 5), 2 hours (lane 6) and 1 hour (lane 7). Lane 8 contains a pre-induction sample. Lane 9 contains the kaleidoscope protein marker.

Figure 7:
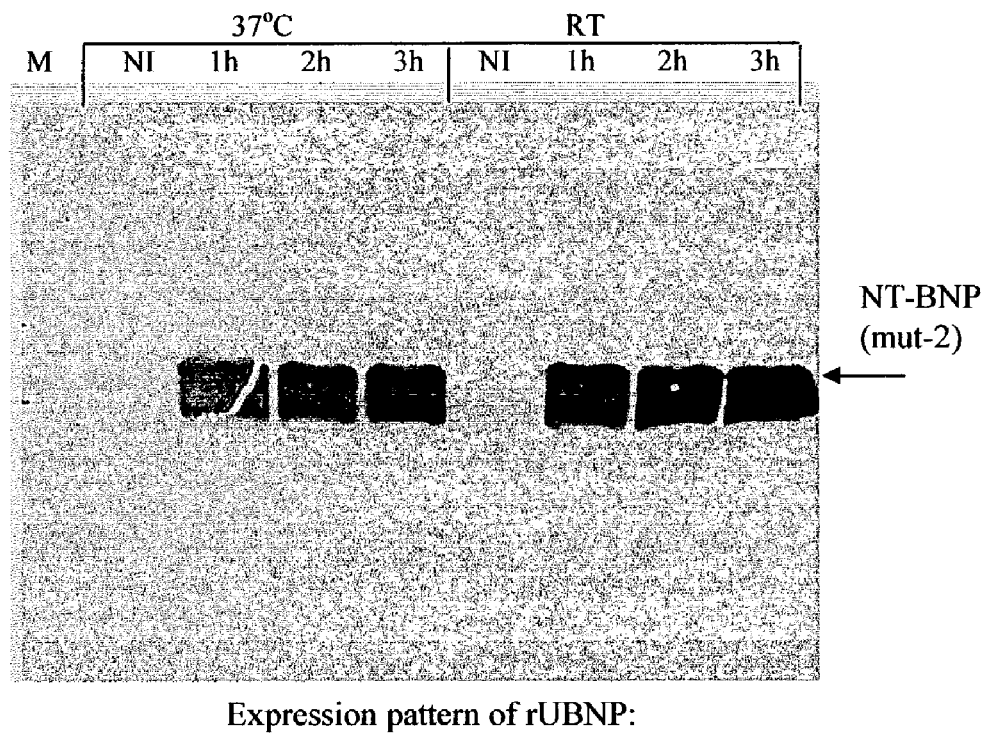
FIG. 7 shows the expression pattern of rUBNP (NT-BNP mut$^{-2}$) visualized using western blotting after 20% SDS PAGE gel electrophoresis.

Western blot analysis with anti-proBNP antibodies confirmed that the induced band is NT-BNP mut$^{-2}$. FIG. 7 exemplifies this result and shows the expression of rUBNP (NT-BNP mut$^{-2}$) by western blotting after 20% SDS-PAGE gel electrophoresis. With regard to FIG. 7, pre and post-induction cell lysate samples were loaded onto the gel. Lane 1 contains the kaleidoscope protein marker. Lane 2 contains a pre-induction sample. Lanes 3-5 contain IPTG induced (at 37° C.) samples from time points 1 hour (lane 3), 2 hours (lane 4) and 3 hours (lane 5). Lane 6 contains a pre-induction sample. Lanes 7-9 contain IPTG induced (at room temperature) samples from time points 1 hour (lane 7), 2 hours (lane 8) and 3 hours (lane 9).

With expression levels of NT-BNP mut$^{-2}$ or rUBNP (3-76 amino acid residues) high enough for purification, a one step FPLC™ (Amersham Pharmacia; fast performance liquid chromatography) based purification method was carried out using SP Sepharose (cation exchange) resin. It is advantageous to use FPLC™ rather than affinity chromatography (used in purification of tagged proteins) since affinity chromatography uses chemicals that can alter the protein conformation and activity.

IPTG induction of 1 liter of bacterial culture yielded approximately 5-7 mg of purified NT-BNP mut$^{-2}$ (rUBNP) protein which can be used to calibrate immunoassays specific for NT-BNP.

Several experiments were conducted to analyze the purified NT-BNP mut$^{-2}$ (rUBNP) protein, the results of these experiments are exemplified in FIGS. 8-11.

Figure 8:
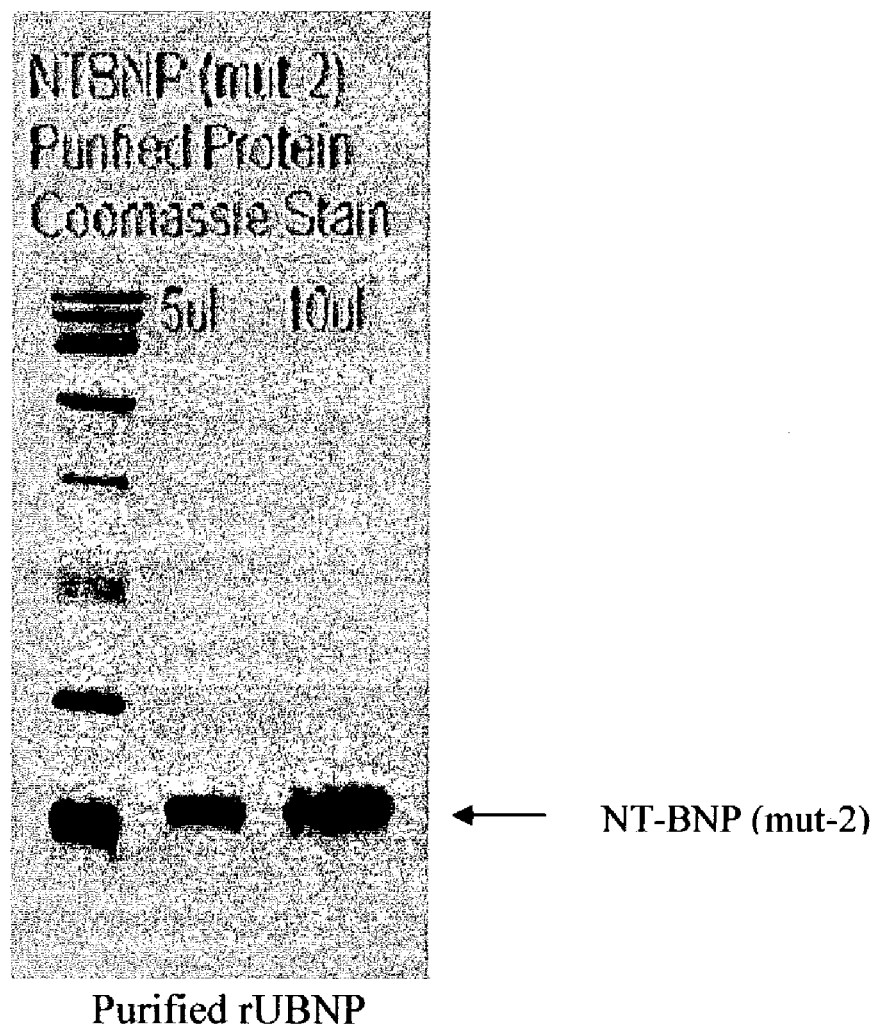
FIG. 8 shows purified rUBNP (NT-BNP mut$^{-2}$) visualized using coomassie staining after 20% SDS PAGE gel electrophoresis.

FIG. 8 shows purified rUBNP visualized by coomassie staining after 20% SDS PAGE gel electrophoresis. With regard to FIG. 8, 0.2 mg/ml purified rUBNP was loaded onto the gel. Lane 1 contains unstained broad range protein marker (BioRad). Lane 2 contains 1ug total purified rUBNP. Lane 3 contains 2 ug total purified rUBNP.

Figure 9:
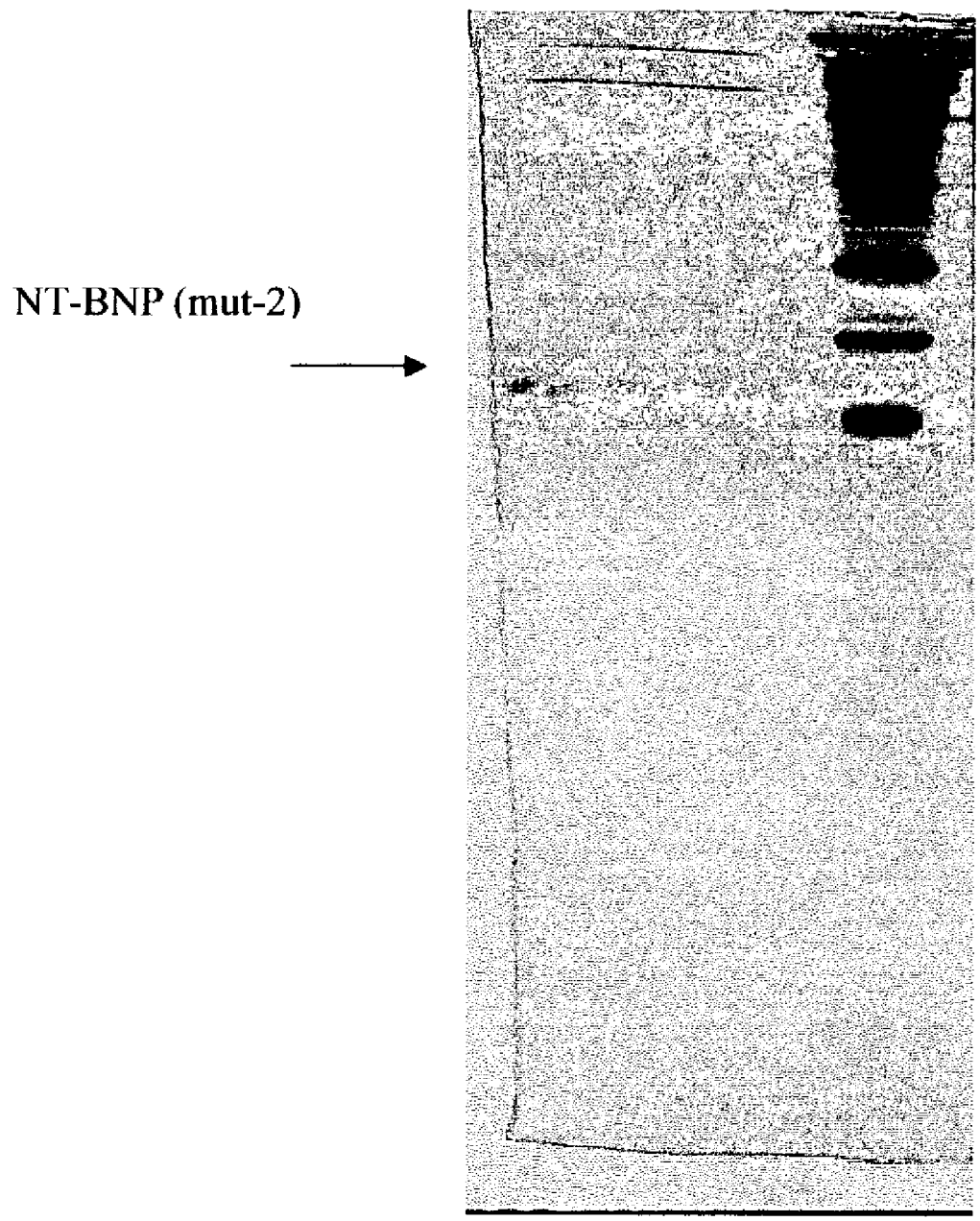
FIG. 9 shows purified rUBNP (NT-BNP mut$^{-2}$) visualized using silver staining after 20% SDS PAGE gel electrophoresis.

FIG. 9 shows purified rUBNP visualized by silver staining after 20% SDS PAGE gel electrophoresis. With regard to FIG. 9, 0.2 mg/ml purified rUBNP was loaded onto the gel. Lane 1 contains unstained broad range protein marker. Lane 2 contains 2 ug total purified rUBNP.

A 9.1 kd band and a 9.3 kd band were identified by coomassie staining. By weight alone these bands can be identified as belonging to NT-BNP, however any protein with the same weight may appear in these bands. In order to be certain that the bands identified are indeed NT-BNP, NT-BNP mut$^{-2}$ was first probed with affinity purified polyclonal antibodies against 3 peptide regions of proBNP (results in FIG. 10) and then sequenced by mass spectrometry (results in FIG. 11).

Figure 10:
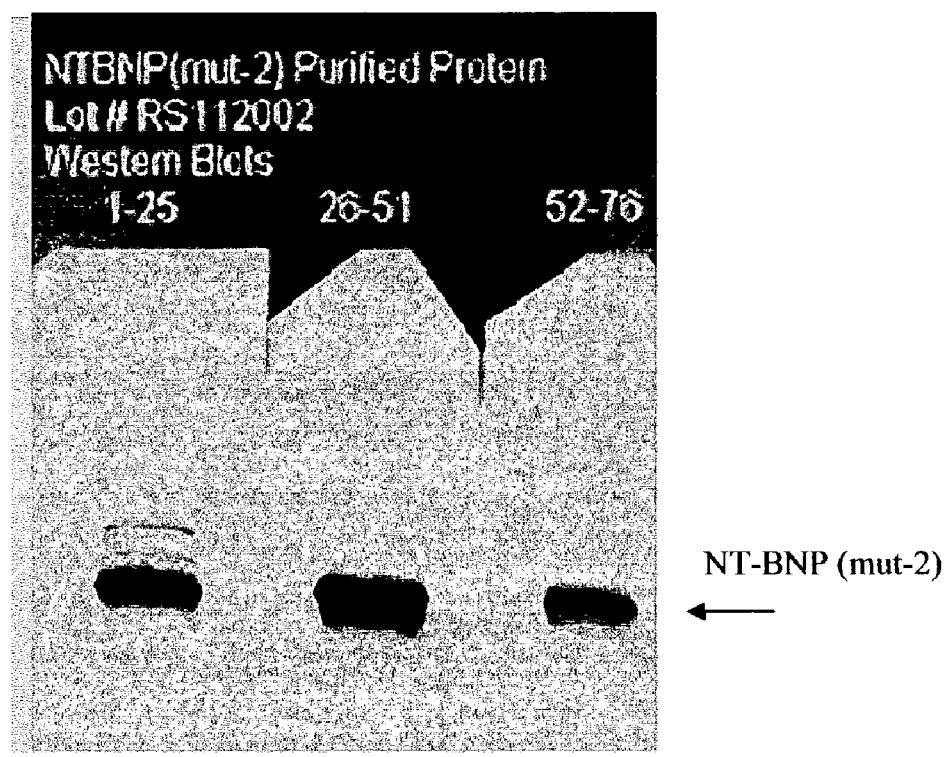
FIG. 10 shows purified NT-BNP mut$^{-2}$ (rUBNP) on a western blot probed with affinity purified polyclonal antibodies against three peptide regions of proBNP after 20% SDS PAGE gel electrophoresis.

FIG. 10 shows the expression of NT-BNP mut$^{-2}$ (rUBNP) visualized by western blotting after 20% SDS PAGE gel electrophoresis. A 2 ug sample of purified NT-BNP mut$^{-2}$ was probed with affinity purified polyclonal antibodies against 3 peptide regions of proBNP; blot 1 (left) shows amino acid region 1-25, blot 2 (center) shows amino acid region 26-51 and blot 3 (right) shows amino acid region 52-76. Primary antibodies were diluted 1:5000 and the secondary antibody (donkey anti-goat HRP) was diluted 1:2000.

Figure 11:
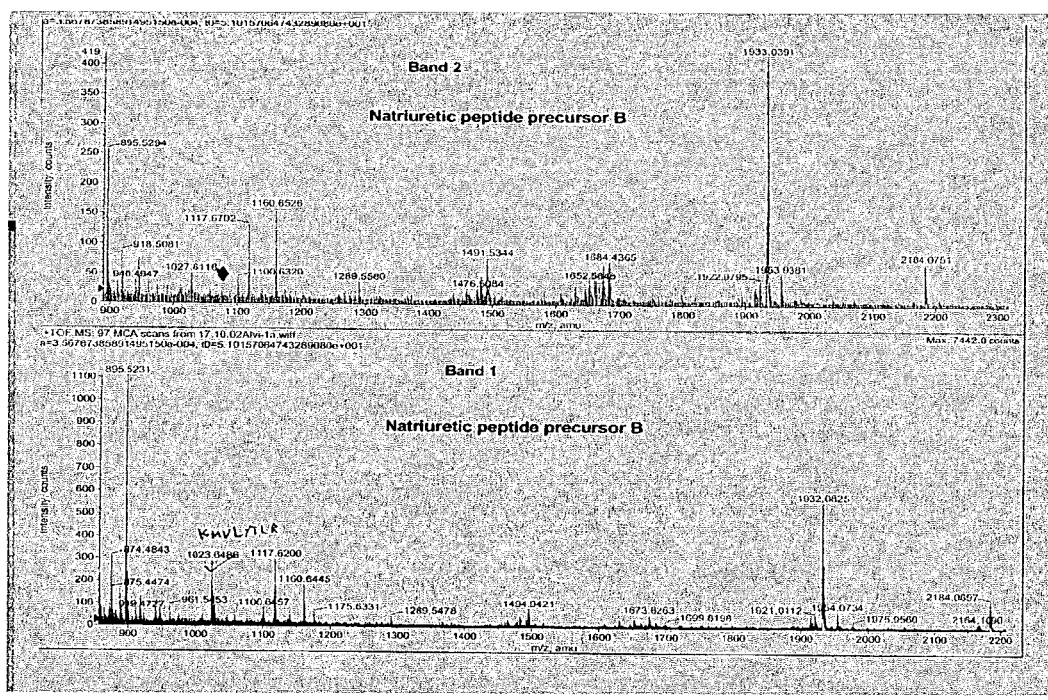
FIG. 11 shows sequencing of the purified NT-BNP mut$^{-2}$ (rUBNP) using mass spectrometry.

FIG. 11 shows sequencing of the NT-BNP mut$^{-2}$ using mass spectrometry. A 9.1 kd band and a 9.3 kd band were identified by coomassie staining. Band 2 (top) 9.1 kd and Band 1 (bottom) 9.3 kd were analyzed. All major peaks were identified as belonging to NT-proBNP. The N-terminus for both bands is intact indicating that there has been no degradation from the N-terminal. The instant inventors are not certain where the degradation exists however only degradation from the N-terminal will effect the immunoassays for which NT-BNP mut$^{-2}$ is used as calibrator.

All of the methods used in steps I-V are known to affect the efficiency of translation initiation in bacteria and when applied singularly or in combination are expected to improve protein expression. However when applying the techniques of steps I-IV, the instant inventors discovered that the amount of NT-BNP mut expression absent histidine tagging was insufficient to efficiently purify. Thus, the method of step V was added to the cloning strategy in an effort to promote an increase in protein expression. The instant inventors have discovered that in order to achieve high-level expression of an untagged NT-BNP protein in bacteria it is necessary to perform the sequence of steps (steps I-V) as claimed in the instant invention.

The instant inventors have thus provided a stepwise method to express an untagged NT-BNP protein (3-76 amino acid residues, NT-BNP mut$^{-2}$ or rUBNP) in *E. coli* that can be purified by one step ion exchange chromatography at greater than 90% purity with a yield of 5-9 mg protein purified/liter of grown culture. This purified NT-BNP mut$^{-2}$ protein is capable of functioning as a calibrator in immunoassays specific for NT-proBNP such as those immunoassays disclosed in co-pending application Ser. Nos. 10/299,977 and 10/300,733 both filed on Nov. 18, 2002. As far as is known to the instant inventors, this is the first report of expression of untagged NT-BNP in bacteria. Furthermore, the expressed protein is not the full length 1-76 amino acid residue NT-BNP protein but a mutated 3-76 amino acid residue NT-BNP protein that is recognized by antibodies directed toward various regions of native NT-proBNP, such as NT-BNP polyclonal antibodies directed at the 1-25 amino acid residue region of NT-BNP as well as polyclonal antibodies specific for the 26-52 amino acid residue region and the 52-76 amino acid residue region.

All patents and publications mentioned in this specification are indicative of the levels of those skilled in the art to which the instant invention pertains. All patents and publications are herein incorporated by reference to the same extent as if each individual patent and publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification.

One skilled in the art will readily appreciate that the present invention is well adapted to carry out the objects and obtain the ends and advantages mentioned, as well as those inherent therein. The oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A stepwise method for expression of NT-BNP (N-terminus brain natriuretic peptide) in *Escherichia coli* (*E. coli*) without an N-terminal histidine affinity chromatography tag for purification comprising sequentially:
   a) introducing SEQ ID NO:1 at the 5' end of a nucleic acid encoding for NT-BNP;
   b) replacing codons 3 through 12 of said nucleic acid encoding for NT-BNP of step a with SEQ ID NO:2;
   c) deleting codons 1 and 2 of said nucleic acid encoding for NT-BNP of step b; and
   d) transfecting an *E. coli* culture with the nucleic acid of step c wherein said *E. coli* culture then expresses NT-BNP without said affinity chromatography based tag for purification.

2. The method of claim 1 further comprising purifying said NT-BNP from said *E. coli* culture.

3. The method of claim 2 wherein said purifying is carried out by fast/performance liquid chromatography (FPLC).

4. The method of claim 1 wherein the NT-BNP is an N-terminal fused peptide that comprises a mutated phage T7 gene 10-translation initiation region and does not include any other N-terminus affinity chromatography tag for purification.

5. A method for expressing a NT-BNP (N-terminus brain natriuretic peptide) in *Escherichia coil* (*E. coli*) without an N-terminal histidine affinity chromatography tag for purification, the method comprising:
   a) constructing an expression plasmid, the expression plasmid comprising, in contiguously linked sequence, SEQ ID NO:1, SEQ ID NO:2, and the nucleic acid sequence encoding N-terminal brain naturetic peptide from codon 13 to codon 76; and
   b) transfecting an *E. coli* culture with the expression plasmid of step a wherein said *E. coli* culture then expresses NT-BNP.

* * * * *